(12) United States Patent
Stasz et al.

(10) Patent No.: US 6,551,256 B1
(45) Date of Patent: Apr. 22, 2003

(54) SNORE SENSOR

(75) Inventors: Peter Stasz, St. Paul, MN (US); Sheri L. Brewer, Lino Lakes, MN (US)

(73) Assignee: Dymedix Corporation, Minneapolis, MN (US)

( * ) Notice: Subject to any disclaimer, the term of this patent is extended or adjusted under 35 U.S.C. 154(b) by 0 days.

(21) Appl. No.: 09/634,148

(22) Filed: Aug. 8, 2000

(51) Int. Cl.$^7$ ................................................ A61B 7/00
(52) U.S. Cl. ...................................................... 600/586
(58) Field of Search ................................ 600/383, 386, 600/388, 391, 586

(56) References Cited

U.S. PATENT DOCUMENTS

| | | | |
|---|---|---|---|
| 4,748,672 A | * 5/1988 | Nevill, Jr. et al. | 382/1 |
| 4,986,277 A | * 1/1991 | Sackner | 600/485 |
| 5,311,875 A | 5/1994 | Stasz | |
| 6,240,323 B1 | * 5/2001 | Calenzo, Sr. et al. | 607/142 |
| 6,341,230 B1 | * 1/2002 | Kioke et al. | 600/392 |

* cited by examiner

Primary Examiner—Max F. Hindenberg
Assistant Examiner—Pamela L Wingood
(74) Attorney, Agent, or Firm—Thomas J. Nikolai; Nikolai & Mersereau

(57) ABSTRACT

A snore sensor incorporating a piezoelectric polyvinylidene fluoride (PVDF) film material adapted to be adhered to the skin of a sleeping patient on the patient's throat for detecting mechanical vibrations due to snoring. The PVDF film has a layer of metallization on opposed major surfaces thereof which are insulated from one another by the PVDF material itself and elongated electrical leads individually connect to the metallization layers. One major surface of the film layer is covered by a layer of adhesive tape and the opposite major surface with its metallization is underlayed by a thin layer of plastic film having an adhesive on opposed surfaces thereof. The adhesive on one side of the plastic film layer adheres it to the PVDF film while the adhesive on the opposed major surface of the plastic film is used to adhere the device to the patient's skin.

5 Claims, 2 Drawing Sheets

SNORE SENSOR

BACKGROUND OF THE INVENTION

I. Field of the Invention

This invention relates generally to biomedical apparatus for use in sleep pattern analysis, and more particularly to a vibration transducer for producing an electrical output signal relating to snoring activity of a sleeping patient.

II. Discussion of the Prior Art

In the Stasz U.S. Pat. No. 5,311,875, there is described a sensing transducer utilizing both the piezoelectric and pyoelectric properties of polyvinylidene fluoride (PVDF) film material which, when appropriately mounted on a sleeping patient's upper lip, will produce a composite output signal relating to temperature changes due to the impingement of respiratory air on the sensor and mechanical vibration due to snoring. The two signals, being of significantly different frequencies, can easily be isolated using electrical filtering techniques.

While the sensor device described in the aforereferenced Stasz patent, the content of which is incorporated by reference herein, works well with many patients, but cannot effectively be used by adult males who happen to have a moustache. Placing the sensor of the Stasz patent on a moustache serves to greatly dampen vibrational energy occasioned by snoring from reaching the PVDF film transducer. Accordingly, a need exists for an improved vibration sensing transducer apparatus that can be used with mustached patients.

SUMMARY OF THE INVENTION

The transducer of the present invention comprises a planar layer of PVDF film material having first and second major surfaces, each having a pattern of metallization thereon. A first electrically conductive lead is attached at a first terminal to the pattern of metallization on the first major surface while a second electrically conductive lead is attached at a second terminal to the pattern of metallization on the second major surface. A fabric layer is adhesively bonded to the planar layer of PVDF material in covering relation to the pattern of metallization on the first major surface and the first terminal. A thin plastic film layer is adhesively adhered to the layer of PVDF material in covering relation to the pattern of metallization on the second major surface and the second terminal. The thin plastic film layer includes an adhesive coating on an undersurface thereof allowing the transducer to be adhesively affixed to the skin of the patient. Specifically, and in accordance with a method described, the transducer is adapted to be affixed to the skin on the neck of a patient for developing an electrical signal proportional to a snoring level of a sleeping patient.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
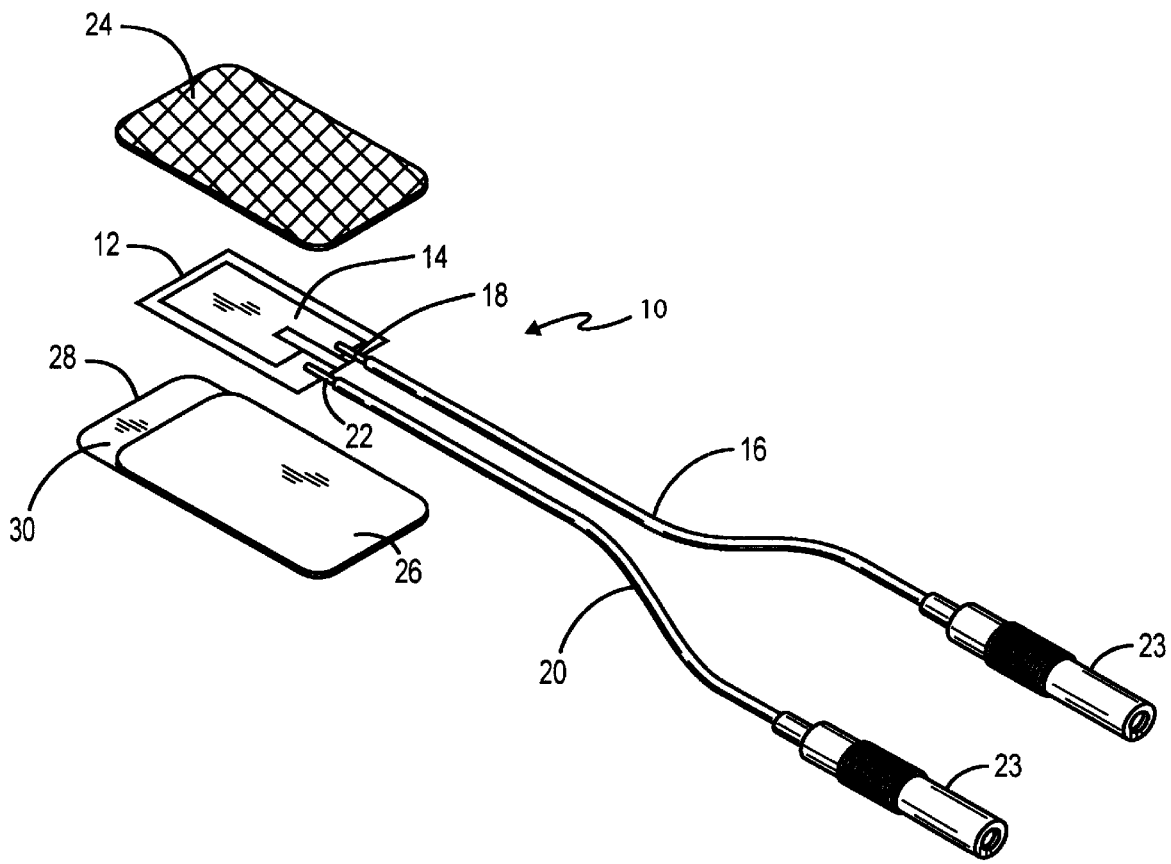
FIG. 1 is an exploded perspective view of the transducer constructed in accordance with the present invention.
Figure 2:
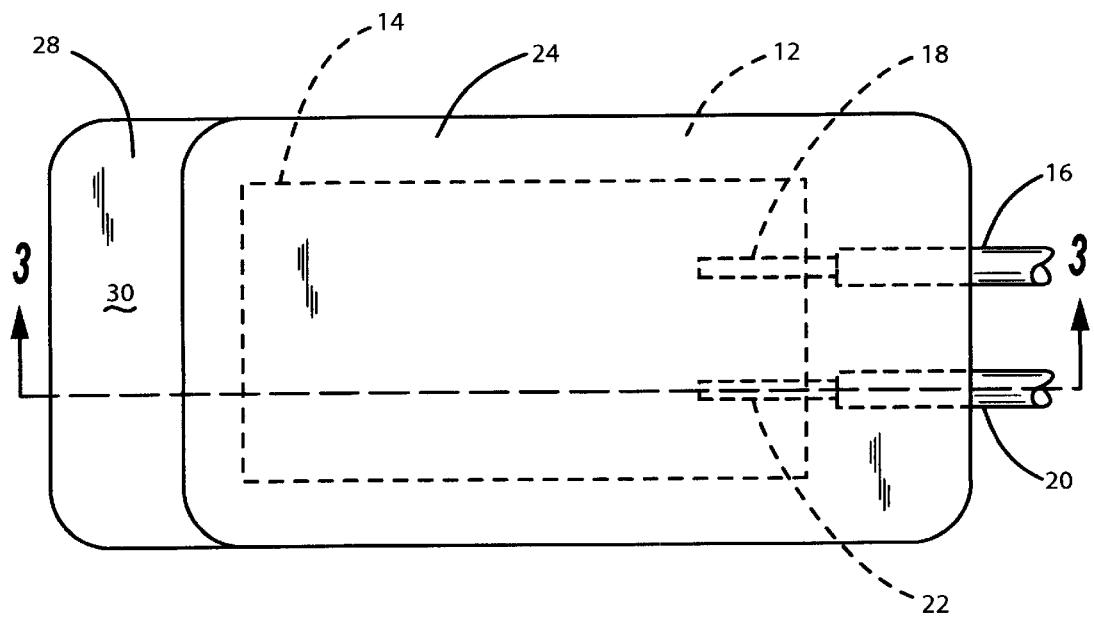
FIG. 2 is a top planar view of the transducer of FIG. 1.
Figure 3:
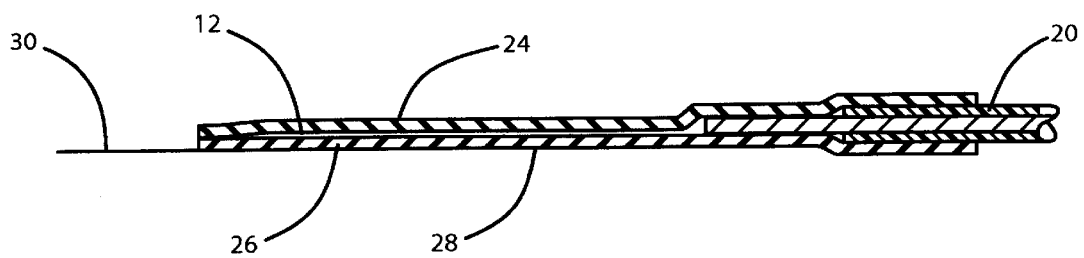
FIG. 3 is a cross-sectional view taken along the line 3—3 in FIG. 2.

Referring to FIGS. 1–3, there is indicated generally by numeral 10 a transducer for converting mechanical vibrational energy to an electrical signal proportional thereto. The transducer comprises a generally planar layer 12 of polyvinylidene fluoride (PVDF) film which, without limitation, may be approximately 1" in length and ½ in width and about 10 mils thick. The sheet 12 has upper and lower major surfaces. Vacuum-deposited, electroplated or otherwise formed on each of the upper and lower major surfaces is a pattern of metallization, such as the metallization layer 14 formed on the upper major surface of the film 12. A similar pattern of metallization is formed on the undersurface of the PVDF film layer 12. A first elongated conductor lead 16 has a distal end 18 thereof soldered to a terminal that makes electrical contact only with the pattern of metallization 14 on the upper surface of the film 12. In a similar fashion, an elongated conductor 20 has its distal end 22 affixed to a terminal that makes electrical contact only with the pattern of metallization on the undersurface of the film layer 12.

The conductors 16 and 20 are each provided with an electrical terminal 23 at a proximal end thereof that is adapted to connect to an electronics module, such as that described in the aforereferenced Stasz patent.

A layer of adhesive tape 24 is applied to the PVDF film layer 12 in covering relation to the metallization layer 14. The adhesive tape layer 24 preferably comprises a tricot fabric whose undersurface is coated with an aggressive adhesive for firmly adhering the tape to the PVDF film. The adhesive tape layer 24 is dimensioned so as to also cover the end portion 18 of the conductor 16 and the terminal to which it is attached.

Bonded to the undersurface of the film layer 12 and in covering relation to the pattern of metallization on that undersurface is a thin film of insulative plastic 26 having an adhesive coating on both the upper and lower surfaces thereof. The adhesive on the upper surface of the film layer 26 allows it to be adhered to the PVDF film material. It is also dimensioned so as to be in covering relation to the metallization layer on the undersurface of the PVDF layer 12 and to the terminal to which the distal end 22 of the lead 20 is connected.

The adhesive on the undersurface of the film layer 26 allows the assembly to be readily attached to the skin of a patient at a desired location while at the same time preventing the skin (a relatively good conductor) from shorting the device's terminals together. The plastic layer 26 is preferably less than about 2.5 mils thick so as not to unduly dampen the vibratory forces reaching the PVDF film layer, thus ensuring a robust voltage output signal.

To protect the adhesive surface on the underside of the film layer 26 during packaging and storage, there is provided a sheet of release paper 28. It has an exposed tab portion 30 that is free of adhesive, permitting it to be grasped between the thumb and forefinger when peeling the release paper sheet 28 from the transducer assembly to expose the adhesive on the undersurface of the film layer 26.

In use, a person will remove the transducer and leads from a package (not shown) and then grasp the tab 30 on the release paper layer 28 and pull the release paper layer free of the transducer to expose the adhesive on the undersurface of the thin plastic film 26. The transducer will then be placed on the skin of the patient proximate the patient's throat. It will be held in place by the adhesive. The leads 16 and 20 will then have their terminals 23 connected to an electronics module. When the patient begins to snore, vibration is imparted to the throat and, through the thin film layer 26 to the PVDF film. Because of its piezoelectric properties, the vibratory motion will result in an electrical signal being produced that is proportional in its amplitude to the level of snoring intensity of the patient. Following amplification and filtering by the electronics module (not shown), the resulting waveform can be displayed on a display screen or, alternatively, digitized and applied to a microprocessor-based analyzer for consideration by a medical professional.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of generating an electrical signal proportional to a snoring level of a sleeping patient, comprising the steps of:

(a) providing a flat, flexible, contact vibration transducer for producing an electrical signal in response to mechanical vibration thereof; and (b) adhesively affixing the contact vibration transducer to the skin on the patient's throat, where said transducer conforms to the contour of the throat surface on which the transducer is affixed.

2. A method of generating an electrical signal proportional to a snoring level of a sleeping patient, comprising the steps of:

(a) providing a flat, flexible, contact vibration transducer for generating an electrical signal proportional to a level of vibration thereof, the transducer comprising a PVDF film layer having first and second major surfaces, each having a pattern of metallization deposited thereon, the pattern of metallization on the first major surface being underlayed with a fabric adhesive tape and the pattern of metallization on the second major surface being overlaid with a rectangular layer of plastic film of a predetermined thickness, the layer of plastic film having rounded corners and a first adhesive coating for adhering the layer of plastic film to the pattern of metallization on the second major surface and a body compatible adhesive coating for adhering the transducer to a patient's skin; and (b) affixing the transducer to the skin of the patient proximate an area on the throat of the patient using the body compatible adhesive coating such that the transducer conforms to the throat surface at said area.

3. The method of claim 2 wherein the contact vibration transducer further includes a layer of release paper covering the body compatible adhesive coating for adhering the transducer to the patient's skin and the method further includes the step of:

(c) removing the layer of release paper to expose the body compatible adhesive coating before affixing the transducer to the skin of the patient.

4. The method as in claim 2 wherein the layer of palstic film is about 2.5 mils in thickness.

5. The method of claim 2 wherein the contact vibration transducer further includes a first elongated conductor connected at a terminal point to the pattern of metallization on the first major surface and a second elongated conductor connected at a terminal point to the pattern of metallization on the second major surface and the layer of plastic film shields the terminal point from contact with the patient's skin and the method includes a further step of attaching the first and second elongated conductors to a signal analyzer.

* * * * *